(12) United States Patent
Rosenblum et al.

(10) Patent No.: US 7,169,557 B2
(45) Date of Patent: Jan. 30, 2007

(54) UNIVERSAL NUCLEOTIDES FOR NUCLEIC ACID ANALYSIS

(75) Inventors: Barnett B. Rosenblum, San Jose, CA (US); Geun-Sook Jeon, Foster City, CA (US); Shaheer H. Khan, Foster City, CA (US)

(73) Assignee: Applera Corporation, Foster City, CA (US)

(*) Notice: Subject to any disclaimer, the term of this patent is extended or adjusted under 35 U.S.C. 154(b) by 431 days.

(21) Appl. No.: 10/290,672

(22) Filed: Nov. 7, 2002

(65) Prior Publication Data

US 2003/0119040 A1 Jun. 26, 2003

Related U.S. Application Data

(60) Provisional application No. 60/336,966, filed on Nov. 7, 2001.

(51) Int. Cl.
*C12Q 1/68* (2006.01)
*C12P 19/34* (2006.01)

(52) U.S. Cl. .................... 435/6; 435/91.2; 435/975

(58) Field of Classification Search ............... 435/6, 435/89, 975; 536/23.1, 24.3
See application file for complete search history.

(56) References Cited

U.S. PATENT DOCUMENTS

| | | | |
|---|---|---|---|
| 5,075,217 A | 12/1991 | Weber | |
| 5,185,144 A | 2/1993 | Koslo et al. | |
| 5,364,759 A | 11/1994 | Caskey et al. | |
| 5,378,841 A | 1/1995 | Summerton et al. | |
| 5,432,272 A | 7/1995 | Benner | |
| 5,470,967 A | 11/1995 | Huie et al. | |
| 5,681,702 A | 10/1997 | Collins et al. | |
| 5,681,947 A | 10/1997 | Bergstrom et al. | |
| 5,698,685 A | 12/1997 | Summerton et al. | |
| 5,719,262 A | 2/1998 | Buchardt et al. | |
| 5,817,781 A | 10/1998 | Swaminathan et al. | |
| 5,858,671 A | 1/1999 | Jones | |
| 5,990,479 A | 11/1999 | Weiss et al. | |
| 6,017,702 A * | 1/2000 | Lee et al. ................ | 435/6 |
| 6,028,190 A * | 2/2000 | Mathies et al. ........... | 536/26.6 |
| 6,043,060 A | 3/2000 | Imanishi | |
| 6,090,558 A | 7/2000 | Butler et al. | |
| 6,107,061 A | 8/2000 | Johnson | |
| 6,124,092 A | 9/2000 | O'Neill et al. | |
| 6,127,121 A | 10/2000 | Meyer et al. | |
| 6,143,877 A | 11/2000 | Meyer et al. | |
| 6,207,392 B1 | 3/2001 | Weiss et al. | |
| 6,221,598 B1 | 4/2001 | Schumm et al. | |
| 6,221,604 B1 * | 4/2001 | Upadhya et al. ........... | 435/6 |
| 6,239,159 B1 | 5/2001 | Brown et al. | |
| 6,268,490 B1 | 7/2001 | Imanishi | |
| 2001/0004728 A1 | 6/2001 | Preparata et al. | |

FOREIGN PATENT DOCUMENTS

| | | |
|---|---|---|
| WO | WO 92/20702 A1 | 11/1992 |
| WO | WO 97/01645 * | 1/1997 |
| WO | WO 99/14226 A2 | 3/1999 |
| WO | WO 00/02899 A1 | 1/2000 |
| WO | WO 00/22171 | 4/2000 |
| WO | WO 00/63439 | 10/2000 |
| WO | WO 01/38584 A2 | 5/2001 |

OTHER PUBLICATIONS

Wu, Y. et al., "Efforts toward Expansion of the Genetic Alphabet: Optimization of Interbase Hydrophobic Interactions", J. Am. Chem. Soc., vol. 122, pp. 7621-7632 (Aug. 2000).*
Promega Catalog, "GenePrint Products", pp. 392-395 (1998).*
Lee, L. G. et al., "New energy Transfer dyes for DNA sequencing", Nucl. Acids Res., vol. 25, pp. 2816-2822 (1997).*
Barsky, Daniel et al., "Interaction and Solvation Energies of the Nonpolar DNA Base Analogues and Their Role in Polymerase Insertion Fidelity," *Journal of Biomolecular Structure & Dynamics*, 16(6):1119-1134 (1999).
Benner, Steven A. et al., "Extending Nature's Alphabet—Enzymatic Incorporation of a New Nucleotide Base Pair into DNA and RNA," Abstracts of Papers at the 197th ACS National Meeting of the American Chemical Society, Dallas, TX, Apr. 9-14, 1989.
Berger, Markus et al., "Stable and Selective Hybridization of Oligonucleotides with Unnatural Hydrophobic Bases," *Angew. Chem. Int. Ed.*, 39(16):2940-2942 (2000).
Berger, Markus et al., "Universal bases for hybridization, replication and chain termination," *Nucleic Acids Research*, 28(15):2911-2914 (2000).

(Continued)

*Primary Examiner*—Teresa E. Strzelecka
(74) *Attorney, Agent, or Firm*—Finnegan, Henderson, Farabow, Garrett & Dunner, LLP

(57) ABSTRACT

The invention includes methods and kits for making and analyzing primer extension products incorporating one or more universal bases, including methods and kits for nucleic acid sequencing and microsatellite analysis.

10 Claims, 2 Drawing Sheets

OTHER PUBLICATIONS

Bergstrom, Donald E. et al., "Comparsion of the base pairing properties of a series of nitroazole nucleobase analogs in the oligodeoxyribonucleotide sequence 5'-d(CGCXAATTYGCG)-3'," *Nucleic Acids Research*, 25(10):1935-1942 (1997).

Dzantiev, Leonid et al., "Significance of Nucleobase Shape Complementarity and Hydrogen Bonding in the Formation and Stability of the Closed Polymerase—DNA Complex," *Biochemistry*, 40:3215-3221 (2001).

Freier, Susan M. et al., "The ups and downs of nucleic acid duplex stability: structure-stability studies on chemically-modified DNA:RNA duplexes," *Nucleic Acids Research*, 25(22):4429-4443 (1977).

Geada, Helena et al., "Portuguese population and paternity Investigation studies with a multiplex PCR—the AmpFISTR® Profiler Plus™," *Forensic Science International*, 108:31-37 (2000).

Han, Mingyong et al., "Quantum-dot-tagged microbeads for multiplexed optical coding of biomolecules," *Nature Biotechnology*, 19:631-635 (2001).

Jeffreys, Alec J. et al., "Repeat Unit Sequence Variation in Minisatellites: A Novel Source of DNA Polymorphism for Studying Variation and Mutation by Single Molecule Analysis," *Cell*, 60:473-485 (1990).

Jones, Robert J. et al., "Synthesis and Binding Properties of Pyrimidine Oligodeoxynucleoside Analogs Containing Neutral Phosphodiester Replacements: The Formacetal and 3'-Thioformacetal Internucleoside Linkages," *J. Org. Chem.*, 58:2983-2991 (1993).

Kool, Eric T., "Replication of Non-hydrogen Bonded Bases by DNA Polymerases: A Mechanism for Steric Matching," *Biopolymers (Nucleic Acid Sciences)*, 48:3-17 (1998).

Krauch, Tilman et al., "New Base Pairs for DNA and RNA," Abstracts of Papers at the 196th ACS National Meeting of the American Chemical Society, Los Angeles, CA, Sep. 25-30, 1988.

Loakes, David, "Survey and Summary: The applications of universal DNA base analogues," *Nucleic Acid Research*, 29(12):2437-2447 (2001).

McMinn, Dustin L. et al., "Efforts toward Expansion of the Genetic Alphabet: DNA Polymerase Recognition of a Highly Stable, Self Pairing Hydrophobic Base," *J. Am. Chem. Soc.*, 121:11585-11586 (1999).

Morales, Juan C. et al., "Efficient replication between non-hydrogen-bonded nucleoside shape analogs," *Nature Structural Biology*, 5(11):950-954 (1998).

Moran, Sean et al., "Non-hydrogen bonding 'terminator' nucleosides increase the 3'-end homogeneity of enzymatic RNA and DNA synthesis," *Nucleic Acids Research*, 24(11):2044-2052 (1996).

Moran, Sean et al., "A thymidine triphosphate shape analog lacking Watson-Crick pairing ability is replicated with high sequence selectivity," *Proc. Natl. Acad. Sci. USA*, 94:10506-10511 (1997).

Moxon, E. Richard et al., "DNA Microsatellites: Agents of Evolution?," *Scientific American*, Jan. 72-77(1999).

Nichols, R. et al., "A universal nucleoside for use at ambiguous sites in DNA primers," *Nature*, 369:492-493 (1994).

Nielsen, Peter E. et al., "Sequence-Selective Recognition of DNA by Strand Displacement with a Thymine-Substituted Polyamide," *Science*, 254:1497-1500 (1991).

Ogawa, Anthony K. et al., "Efforts toward the Expansion of the Genetic Alphabet: Information Storage and Replication with Unnatural Hydrophobic Base Pairs," *J. Am. Chem. Soc.*, 122:3274-3287 (2000).

Piccirilli, Joseph A. et al., "Enzymatic incorporation of a new base pair into DNA and RNA extends the genetic alphabet," *Nature*, 343:33-37 (1990).

Sanger, F. et al., "DNA sequencing with chain-terminating inhibitors," *Proc. Natl. Acad. Sci. USA*, 74(12):5463-5467 (1977).

Seela, Frank et al., "The $N^8$-(2'-deoxyribofuranoside) of 8-aza-7-deazaadenine: a universal nucleoside forming specific hydrogen bonds with the four canonical DNA constituents," *Nucleic Acids Research*, 28(17):3224-3232 (2000).

Service, Robert F., "News Focus: Creation's Seventh Day," *Science*, 289:232-235 (2000).

Smith, C.L. et al., "DNA Polymerase Incorporation of Universal Base Triphosphates," *Nucleosides & Nucleotides*, 17(1-3):541-554 (1998).

Stirchak, Eugene P. et al., "Uncharged Stereoregular Nucleic Acid Analogues. 1. Synthesis of a Cystosine-Containing Oligomer with Carbamate Internucleoside Linkages," *J. Org. Chem.*, 52:4202-4206 (1987).

Switzer, Christopher et al., "Enzymatic Incorporation of a New Base Pair into DNA and RNA," *J. Am. Chem. Soc.*, 111:8322-8323 (1989).

Tae, Eunju Lee et al., "Efforts toward Expansion of the Genetic Alphabet: Replication of DNA with Three Base Pairs," *J. Am. Chem. Soc.*, 123:7439-7440 (2001).

Tae, Eunju Lee et al., "Supplementary Information: Efforts Toward Expansion of the Genetic Alphabet: Replication of DNA with Three Base Pairs," *J. Am. Chem. Soc.*, Supporting Info.: pp. 1-5 (2001).

Vasseur, Jean-Jacques et al., "Oligonucleosides: Synthesis of a Novel Methylhydroxylamine-Linked Nucleoside Dimer and Its Incorporation into Antisense Sequences," *J. Am. Chem. Soc.*, 114:4006-4007 (1992).

Wang, David G. et al., "Large-Scale Identification, Mapping, and Genotyping of Single-Nucleotide Polymorphisms in the Human Genome," *Science*, 280:1077-1082 (1998).

Weber, James L. et al., "Abundant Class of Human DNA Polymorphisms Which Can Be Typed Using the Polymerase Chain Reaction," *Am. J. Hum. Genet.*, 44:388-396 (1989).

Weber, James L., "Human DNA Polymorphisms Based on Length Variations in Simple-sequence Tandem Repeats," *Genome Analysis* vol. 1: *Genetic and Physical Mapping*, Cold Spring Harbor Laboratory Press, pp. 159-181 (1990).

Wu, Yiqin, "Efforts toward Expansion of the Genetic Alphabet: Optimization of Interbase Hydrophobic Interactions," *J. Am. Chem. Soc.*, 122(32):7621-7632 (2000).

Zhang, Peiming et al., "Peptide Nucleic Acid-DNA Duplexes Containing the Universal Base 3-Nitropyrrole," *Methods*, 23:132-140 (2001).

*Application Note: Automated Flourescene Detection for Microsatellite Analysis*, Applied Biosystems, pp. 1-4 (1993).

Hoops et al., "Template directed incorporation of nucleotide mixtures using azole-nucleobase analogs," *Nucleic Acids Research*, 25:4866-4871 (1997).

Rosenblum et al., "New dye-labeled terminators for improved DNA sequencing patterns," *Nucleic Acids Research*, 25:4500-4504 (1997).

Communication pursuant to Article 96(2) EPC in European Patent Application No. 02 784 192.3-2402, dated Apr. 6, 2006.

\* cited by examiner (A) d7AiTP (B) dM7AITP (C) dPPTP (D) dImPyTP (E) dICSTP (F) dP7AITP (G) dPICSTP (H) dA7AITP

R=

UNIVERSAL NUCLEOTIDES FOR NUCLEIC ACID ANALYSIS

This application claims the priority benefit of U.S. Provisional Application Ser. No. 60/336,966, filed Nov. 7, 2001. This application incorporates by reference all of the disclosure of U.S. Provisional Application Ser. No. 60/336,966.

FIELD OF THE INVENTION

The present invention generally relates to universal nucleotides that can be incorporated into a polynucleotide strand during nucleic acid synthesis.

BACKGROUND OF THE INVENTION

Primer extension reactions are widely used in modern molecular biology. For example, in Sanger sequencing, an oligonucleotide primer is annealed to a 5' end of a template, and deoxyribonucleotide triphosphates (dNTPs), polymerase, and four dideoxynucleotide terminators are added to form a reaction composition (the four teminators are either added to separate reactions or together in one reaction), and the reaction composition is incubated under appropriate conditions to achieve primer extension and termination.

Analysis of microsatellites, including Variable Number of Tandem Repeats (VNTRs) and Short Tandem Repeats (STRs), is another widely used method employing a primer extension reaction. STRs are sequences of two to seven nucleotides that are tandemly repeated at one or more locations in the genome. The number of tandem repeats varies from individual to individual. For certain genetic analysis techniques, STRs are amplified by PCR using specific primers flanking the repeat region and the number of repeats is determined. In certain techniques, the determination is made using size differentiation, e.g., by electrophoresis, mass spectroscopy, or chromatography.

SUMMARY OF THE INVENTION

In certain embodiments, a method of sequencing at least one target nucleic acid template is provided. Certain such embodiments involve forming a reaction composition comprising at least one target nucleic acid template, at least one primer, at least one polymerase, at least one universal nucleotide, and at least one specific terminator that comprises a label. The reaction composition is incubated to generate at least one primer extension product comprising the at least one universal nucleotide and the at least one specific terminator. One or more of the at least one primer extension products is separated using at least one mobility-dependent analysis technique (MDAT). One or more of the at least one primer extension product is then detected.

In certain embodiments, a method of sequencing at least one target nucleic acid template comprises forming at least one reaction composition that comprises at least one target nucleic acid template, at least one primer comprising a label, at least one polymerase, at least one universal nucleotide, and at least one specific terminator. The reaction composition is incubated to generate at least one primer extension product comprising one or more of the at least one universal nucleotides and one or more of the at least one specific terminators. One or more of the at least one primer extension product is separated using at least one mobility-dependent analysis technique (MDAT). One or more of the at least one primer extension products is then detected.

In certain embodiments, the method of sequencing at least one target nucleic acid template further comprises releasing the at least one primer extension product from the at least one target nucleic acid template, and repeating the incubating and releasing at least one additional time.

Certain embodiments of the invention provide a method for detecting a plurality of primer extension products. According to certain embodiments, the method includes forming a reaction composition comprising at least one template, at least one primer comprising a label, at least one polymerase, and at least one universal nucleotide. The reaction composition is incubated under appropriate conditions to generate at least one primer extension product comprising one or more of the at least one universal nucleotides. The primer extension product is released from the at least one target nucleic acid template, and the incubation and releasing procedures are repeated to produce a plurality of primer extension products. One or more of the plurality of primer extension products are separated using an MDAT. One or more of the plurality of primer extension products are then detected.

According to certain embodiments, a method for detecting a plurality of second primer extension products is provided. In certain embodiments, the method comprises forming a first reaction composition comprising at least one target nucleic acid template, at least one first primer, at least one specific nucleotide, and at least one first polymerase, wherein the first reaction composition does not include universal nucleotides. The first reaction composition is incubated under appropriate conditions to generate at least one first primer extension product. The at least one first primer extension product is released from the at least one target nucleic acid template, and the incubation and releasing procedures are repeated to produce a plurality of first primer extension products. In certain embodiments, the method further comprises forming a second reaction composition comprising one or more of the at least one first primer extension product, at least one second primer comprising a label, at least one second polymerase, and at least one universal nucleotide. The second reaction composition is incubated under appropriate conditions to generate at least one second primer extension product. The at least one second primer extension product is released from the at least one first primer extension product, and the incubation and releasing procedures are repeated to produce a plurality of second primer extension products. In certain embodiments, the method includes separating one or more of the plurality of second primer extension products using an MDAT. One or more of the plurality of second primer extension products are then detected.

According to certain embodiments, a kit is provided for sequencing a target nucleic acid template. In certain embodiments, the kit comprises at least one polymerase, at least one universal nucleotide, and at least one specific terminator.

In certain embodiments, a kit is provided for detecting a short tandem repeat in a target nucleic acid template. In certain embodiments, the kit comprises at least one universal nucleotide, at least one polymerase, and at least one primer comprising a sequence that is complementary to a sequence adjacent to a short tandem repeat in the target nucleic acid template.

BRIEF DESCRIPTION OF THE DRAWINGS

FIG. 1A schematically illustrates primer extension proceeding in the presence of natural nucleotides, e.g., A (dATP), T (dTTP), G (dGTP), and C (dCTP), with a tetranucleotide primer (hatched bar). Each nucleotide adds to the primer extension product (SEQ ID NO: 2) in a template sequence dependent manner, e.g., based on Watson-Crick base pairing wherein A pairs with T, and G pairs with C. In certain exemplary embodiments, shown in FIG. 1B, primer extension in the presence of universal nucleotide "X" results in the incorporation of the universal nucleotide into the primer extension product (SEQ ID NO: 3) in a template sequence-independent manner. Thus, universal nucleotide "X" can pair with any nucleotide present in the template. In certain exemplary embodiments, shown in FIG. 1C, primer extension in the presence of hypothetical universal nucleotide "Z" results in the incorporation of the universal nucleotide into the primer extension (SEQ ID NO: 4) product opposite certain nucleotides in the template, but not for others. Here, for example, Z pairs with a G and C nucleotides in the template, but Z does not pair with A or T. Thus, Z is a universal nucleotide with respect to G and C, but not with respect to A or T. In certain exemplary embodiments, shown in FIG. 1D, primer extension in the presence of hypothetical universal nucleotide "Y" results in the incorporation of the universal nucleotide into the primer extension product (SEQ ID NO: 5) opposite A, T, and C in the template, but not opposite G.

FIG. 2 shows the structures of several non-limiting exemplary universal nucleotides. (A) 2'-deoxy-7-azaindole-5'-triphosphate (d7AITP), (B) 2'-deoxy-6-methyl-7-azaindole-5'-triphosphate (dM7AITP), (C) 2'-deoxy-pyrrollpyrizine-5'-triphosphate (dPPTP), (D) 2'-deoxy-imidizopyridine-5'-triphosphate (dImPyTp), (E) 2'-deoxy-isocarbostyril-5'-triphosphate (dICSTP), (F) 2'-deoxy-propynyl-7-azaindole-5'-triphosphate (dP7AITP), (G) 2'-deoxy-propynylisocarbostyril-5'-triphosphate (dPIC-STP), and (H) 2'-deoxy-allenyl-7-azaindole-5'-triphosphate (dA7AITP). "R", as used in this figure, is the deoxyribose moiety of the nucleotide.

DETAILED DESCRIPTION OF EXEMPLARY EMBODIMENTS

Figure 1:
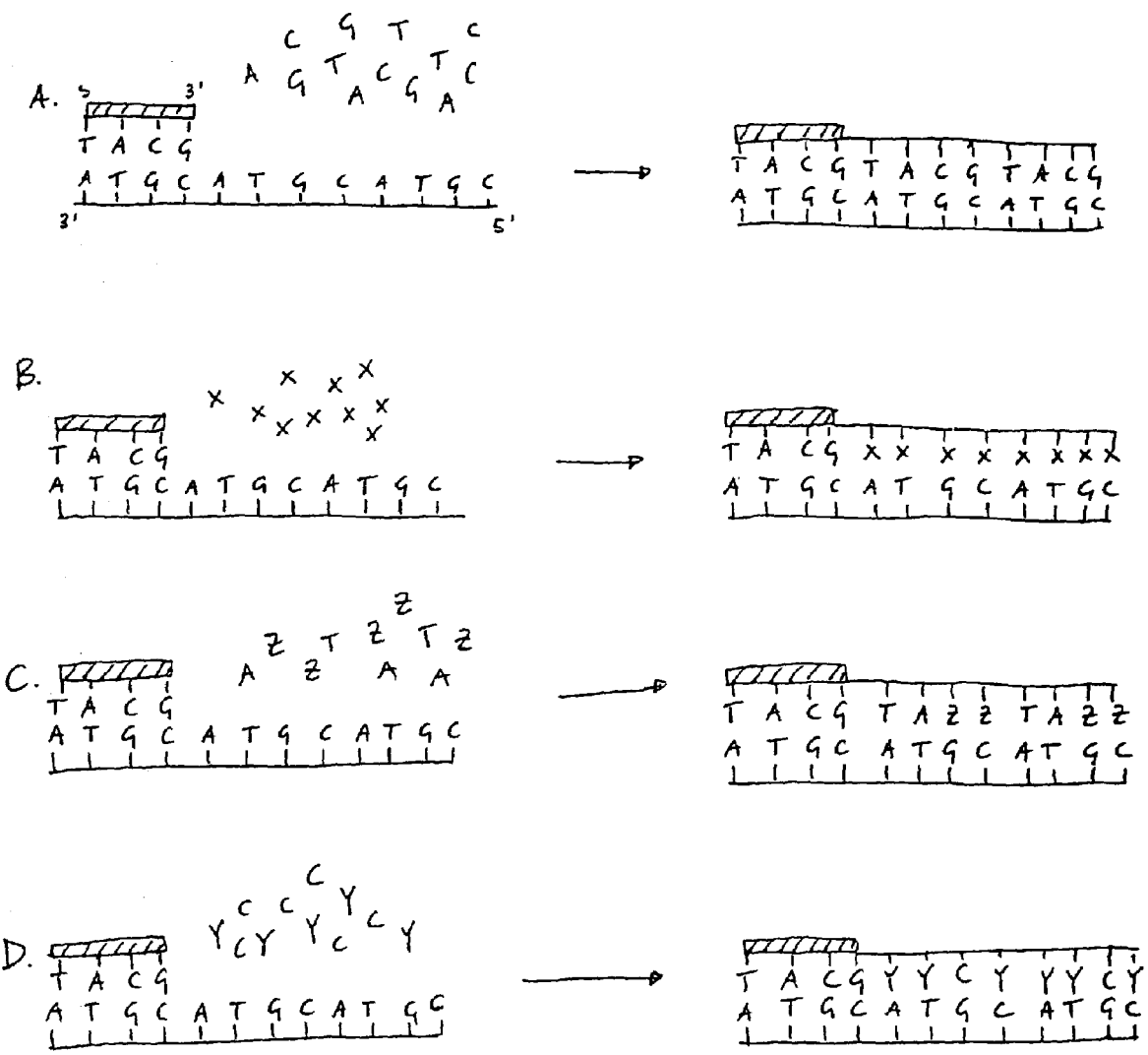
FIG. 1.
Figure 2:
FIG. 2.
Figure 2:
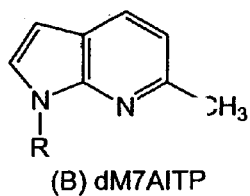
Figure 2:
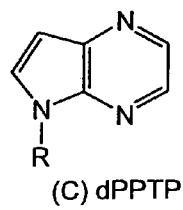
Figure 2:
Figure 2:
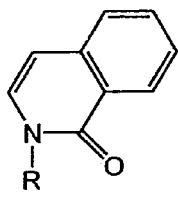
Figure 2:
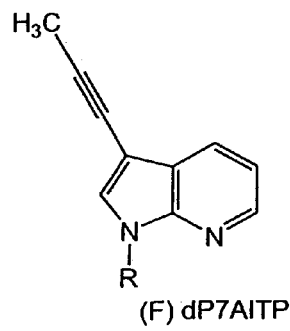
Figure 2:
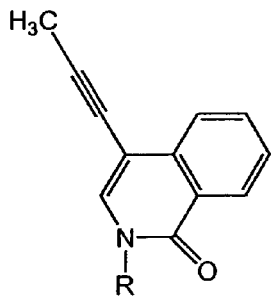
Figure 2:
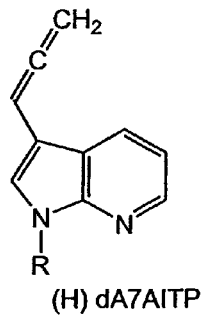
Figure 2:
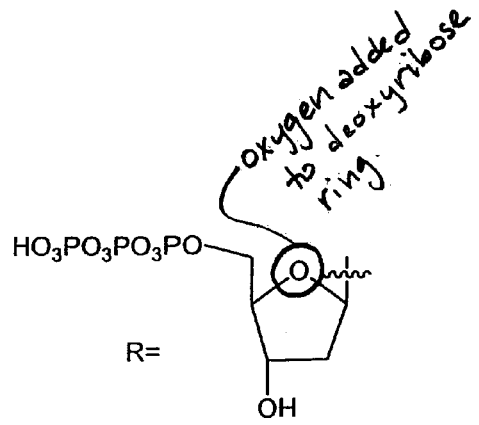

It is to be understood that both the foregoing general description and the following detailed description are exemplary and explanatory only and are not restrictive of the invention. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. In certain embodiments, nucleotide bases are universal nucleotide bases. Certain exemplary nucleotide bases can be found, e.g., in Fasman, 1989, Practical Handbook of Biochemistry and Molecular Biology, pp. 385–394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$–$C_6$ alkyl or $C_5$–$C_{14}$ aryl. Exemplary riboses include, but are not limited to, 2'-($C_1$–$C_6$)alkoxyribose, 2'-($C_5$–$C_{14}$)aryloxyribose, 2',3'-didehydroribose, 2'-deoxy-3'-haloribose, 2'-deo xy-3'-fluororibose, 2'-deoxy-3'-chlororibose, 2'-deoxy-3'-aminoribose, 2'-deoxy-3'-($C_1$–$C_6$)alkylribose, 2'-deoxy-3'-($C_1$–$C_6$)alkoxyribose and 2'-deoxy-3'-($C_5$–$C_{14}$)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352;, and WO 99/14226). Exemplary LNA sugar analogs within a polynucleotide include, but are not limited to, the structures:

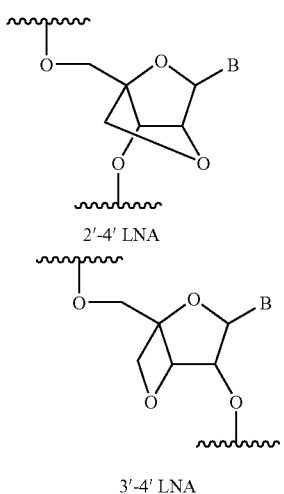

2'-4' LNA

3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159–65; Fujimori (1990) J. Amer. Chem. Soc. 112:

7435; Urata, (1993) Nucleic Acids Symposium Ser. No. 29:69–70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication, 2nd* Ed., Freeman, San Francisco, Calif.).

One or more of the pentose carbons of a nucleotide may be substituted with a phosphate ester having the formula:

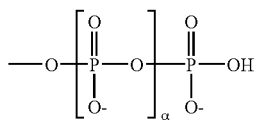

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, a universal nucleotide base, a specific nucleotide base, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see, e.g., Shabarova, Z. and Bogdanov, A. *Advanced Organic Chemistry of Nucleic Acids*, VCH, New York, 1994.

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

An "extendable nucleotide" is a nucleotide which is: (i) capable of being enzymatically or synthetically incorporated onto the terminus of a polynucleotide chain, and (ii) capable of supporting further enzymatic or synthetic extension. Extendable nucleotides include nucleotides that have already been enzymatically or synthetically incorporated into a polynucleotide chain, and have either supported further enzymatic or synthetic extension, or are capable of supporting further enzymatic or synthetic extension. Extendable nucleotides include, but are not limited to, nucleotide 5'-triphosphates, e.g., dNTP and NTP, phosphoramidites suitable for chemical synthesis of polynucleotides, and nucleotide units in a polynucleotide chain that have already been incorporated enzymatically or chemically. Extendable nucleotides include, but are not limited to, specific nucleotides, nucleotide analogs, and universal nucleotides.

The term "type" as used herein with respect to nucleotides, refers to a structurally distinct nucleotide. For example, A and G are different types of nucleotides. Similarly, G and I are different types of nucleotides, although they both may pair with C. Nucleotides that are different "pairing types", as used herein, are both structurally distinct and have different pairing specificities. For example, A and G are different pairing types of nucleotides, because they are structurally distinct, and they have different pairing specificities (T versus C). G and I are not different pairing types of nucleotides when compared to one another, because, although they are structurally distinct, they both pair specifically with C. The pairing type of a universal nucleotide, as defined below, is determined by the combination of nucleotides with which it pairs. For example, hypothetical universal nucleotide Y pairs with A, C, and T, and hypothetical universal nucleotide X, which is structurally distinct from Y, pairs with C and G. X and Y are therefore different types of universal nucleotides, and X and Y are also different pairing types of universal nucleotides, although they both may pair with C.

The term "specific nucleotide", as used herein, refers to an extendable nucleotide that can be incorporated into a polynucleotide strand by a polymerase during a primer extension reaction, and will not pair with more than one different pairing type of nucleotide in a template strand, where the nucleotide in the template strand is not a universal nucleotide. For example, C is a specific nucleotide, even though it pairs specifically with both G and I, since G and I are not different pairing types of nucleotides. Similarly, C is a specific nucleotide, even though it pairs with both G and a universal nucleotide. Specific nucleotides may be naturally-occurring nucleotides, e.g., adenine, cytosine, guanine, thymine or uracil. Specific nucleotides may also be nucleotide analogs that pair in a template sequence-specific manner.

The term "universal nucleotide", as used herein, refers to an extendable nucleotide that can be incorporated into a polynucleotide strand by a polymerase during a primer extension reaction, and pairs with more than one pairing type of specific nucleotide. In certain embodiments, the universal nucleotide pairs with any specific nucleotide. In certain embodiments, the universal nucleotide pairs with four pairing types of specific nucleotides or analogs thereof. In certain embodiments, the universal nucleotide pairs with three pairing types of specific nucleotides or analogs thereof. In certain embodiments, the universal nucleotide pairs with two pairing types of specific nucleotides or analogs thereof. The pairing of a universal nucleotide with two or more pairing types of specific nucleotides will be referred to as non-template sequence-specific pairing.

The terms "universal nucleotide base" and "universal base" are used interchangeably and, as used herein, refer to the base portion of a universal nucleotide. The universal nucleotide base may include an aromatic ring moiety, which may or may not contain nitrogen atoms. In certain embodiments, a universal base may be covalently attached to the C-1' carbon of a pentose sugar to make a universal nucleotide. In certain embodiments, a universal nucleotide base does not hydrogen bond specifically with another nucleotide base. In certain embodiments, a universal nucleotide base may interact with adjacent nucleotide bases on the same nucleic acid strand by hydrophobic stacking. Universal nucleotides include, but are not limited to, 2'-deoxy-7-azaindole-5'-triphosphate (d7AITP), 2'-deoxy-isocarbostyril-5'-triphosphate (dICSTP), 2'-deoxy -propynylisocarbostyril-5'-triphosphate (dPICSTP), 2'-deoxy-6-methyl-7-azaindole-5'-triphosphate (dM7AITP), 2'-deoxy-imidizopyridine-5'-triphosphate (dImPyTp), 2'-deoxy-pyrrollpyrizine-5'-triphosphate (dPPTP), 2'-deoxy-propynyl-7-azaindole-5'-triphosphate (dP7AITP), or 2'-deoxy-allenyl-7-azaindole-5'-triphosphate (dA7AITP).

The term "nucleotide terminator" or "terminator", as used herein, refers to an enzymatically-incorporable nucleotide, which does not support incorporation of subsequent nucleotides in a primer extension reaction. A terminator is therefore not an extendable nucleotide. In certain embodiments, terminators are those in which the nucleotide is a purine, a 7-deaza-purine, a pyrimidine, a specific nucleotide or nucleotide analog and the sugar moiety is a pentose which includes a 3'-substituent that blocks further synthesis, such as a dideoxynucleotide triphosphate (ddNTP). In certain embodiments, substituents that block further synthesis include, but are not limited to, amino, deoxy, halogen, alkoxy and aryloxy groups. Exemplary terminators include, but are not limited to, those in which the sugar-phosphate ester moiety is 3'-(C1–C6)alkylribose-5'-triphosphate, 2'-deoxy-3'-(C1–C6) alkylribose-5'-triphosphate, 2'-deoxy-3'-(C1–C6)alkoxyribose-5-triphosphate, 2'-deoxy-3'-(C5–C14)aryloxyribose-5'-triphosphate, 2'-deoxy-3'-halori-bose-5'-triphosphate, 2'-deoxy-3'-aminoribose-5'triphosphate, 2',3'-dideoxyribose-5'-triphosphate or 2',3'-didehydroribose-5'-triphosphate. In certain embodiments, ddNTPs, such as ddATP, ddCTP, ddGTP, ddITP, and ddTTP, may be used for chain termination.

In certain embodiments, a terminator is a "specific terminator", which is incorporated by polymerase into a primer extension product opposite a particular nucleotide in the template. Specific terminators include, but are not limited to, T terminators, including ddTTP, which incorporate opposite an adenine, or adenine analog, in a template; A terminators, including ddATP, which incorporate opposite a thymine, uracil, or an analog of thymine or uracil, in the template; C terminators, including ddCTP, which incorporate opposite a guanine, or guanine analog, in the template; and G terminators, including ddGTP, which incorporate opposite a cytosine, or cytosine analog, in the template.

The term "label" refers to any moiety which can be attached to a molecule and: (i) provides a detectable signal; (ii) interacts with a second label to modify the detectable signal provided by the second label, e.g. FRET (Fluorescent Resonance Energy Transfer); (iii) stabilizes hybridization, e.g., duplex formation; or (iv) provides a member of a binding complex or affinity set, e.g., affinity, antibody/antigen, ionic complexation, hapten/ligand, e.g. biotin/avidin. Labeling can be accomplished using any one of a large number of known techniques employing known labels, linkages, linking groups, reagents, reaction conditions, and analysis and purification methods. Labels include, but are not limited to, light-emitting or light-absorbing compounds which generate or quench a detectable fluorescent, chemiluminescent, or bioluminescent signal (see, e.g., Kricka, L. in *Nonisotopic DNA Probe Techniques* (1992), Academic Press, San Diego, pp. 3–28). Fluorescent reporter dyes useful for labelling biomolecules include, but are not limited to, fluoresceins (see, e.g., U.S. Pat. Nos. 5,188,934; 6,008, 379; and 6,020,481), rhodamines (see, e.g., U.S. Pat. Nos. 5,366,860; 5,847,162; 5,936,087; 6,051,719; and 6,191, 278), benzophenoxazines (see, e.g., U.S. Pat. No. 6,140, 500), energy-transfer fluorescent dyes, comprising pairs of donors and acceptors (see, e.g., U.S. Pat. Nos. 5,863,727; 5,800,996; and 5,945,526), and cyanines (see, e.g., Kubista, WO 97/45539), as well as any other fluorescent label capable of generating a detectable signal. Examples of fluorescein dyes include, but are not limited to, 6-carboxy-fluorescein; 2',4',1,4,-tetrachlorofluorescein; and 2',4',5',7',1, 4-hexachlorofluorescein. Labels also include, but are not limited to, semiconductor nanocrystals, or quantum dots (see, e.g., U.S. Pat. Nos. 5,990,479 and 6,207,392 B1; Han et al. *Nature Biotech*. 19: 631–635).

A class of labels are hybridization-stabilizing moieties which serve to enhance, stabilize, or influence hybridization of duplexes, e.g. intercalators, minor-groove binders, and cross-linking functional groups (see, e.g., Blackburn, G. and Gait, M. Eds. "DNA and RNA structure" in *Nucleic Acids in Chemistry and Biology*, 2$^{nd}$ Edition, (1996) Oxford University Press, pp. 15–81). Yet another class of labels effect the separation or immobilization of a molecule by specific or non-specific capture, for example biotin, digoxigenin, and other haptens (see, e.g., Andrus, A. "Chemical methods for 5' non-isotopic labeling of PCR probes and primers" (1995) in *PCR 2: A Practical Approach*, Oxford University Press, Oxford, pp. 39–54). Non-radioactive labelling methods, techniques, and reagents are reviewed in: *Non-Radioactive Labelling, A Practical Introduction*, Garman, A. J. (1997) Academic Press, San Diego.

Labels may be "detectably different", which means that they are distinguishable from one another by at least one detection method. Detectably different labels include, but are not limited to, labels that emit light of different wavelengths, labels that absorb light of different wavelengths, labels that have different fluorescent decay lifetimes, labels that have different spectral signatures, labels that have different radioactive decay properties, labels of different charge, and labels of different size.

The term "labeled terminator", as used herein, refers to a terminator that is physically joined to a label. The linkage to the label is at a site or sites on the terminator that do not prevent the incorporation of the terminator by a polymerase into a polynucleotide.

As used herein, the term "target nucleic acid template" refers to a nucleic acid sequence that serves as a template for a primer extension reaction. Target nucleic acid templates include, but are not limited to, genomic DNA, including mitochondrial DNA and nucleolar DNA, cDNA, synthetic DNA, plasmid DNA, yeast artificial chromosomal DNA (YAC), bacterial artificial chromosomal DNA (BAC), and other extrachromosomal DNA, and primer extension products. Target nucleic acid templates also include, but are not limited to, RNA, synthetic RNA, mRNA, tRNA, and analogs of both RNA and DNA, such as peptide nucleic acids (PNA). In certain embodiments, target nucleic acid templates do not contain universal nucleotides.

Different target nucleic acid templates may be different portions of a single contiguous nucleic acid or may be on different nucleic acids. Different portions of a single contiguous nucleic acid may overlap.

"Primer" as used herein refers to a polynucleotide or oligonucleotide that has a free 3'-OH (or functional equivalent thereof) that can be extended by at least one nucleotide in a primer extension reaction catalyzed by a polymerase. In certain embodiments, primers do not contain universal nucleotides. In certain embodiments, primers may be of virtually any length, provided they are sufficiently long to hybridize to a polynucleotide of interest in the environment in which primer extension is to take place. In certain embodiments, primers are at least 14 nucleotides in length. Primers may be specific for a particular sequence, or, alternatively, may be degenerate, e.g., specific for a set of sequences.

The terms "primer extension" and "primer extension reaction" are used interchangeably, and refer to a process of adding one or more nucleotides to a nucleic acid primer, or to a primer extension product, using a polymerase, a template, and one or more nucleotides. In certain embodiments, a primer extension reaction includes at least one universal nucleotide. In other words, it includes at least one type of universal nucleotide, although it may include many molecules of each type of universal nucleotide. In certain embodiments, a primer extension reaction includes one type of universal nucleotide, although it may include many molecules of that type of universal nucleotide.

A "primer extension product" is produced when one or more nucleotides has been added to a primer in a primer extension reaction. In certain embodiments, a primer extension product includes one type of universal nucleotide. In certain embodiments, a primer extension product includes more than one type of universal nucleotide. In certain embodiments, a primer extension product is comprised of a 5' sequence of specific nucleotides followed by one or more universal nucleotides. In certain embodiments, the 5' sequence of specific nucleotides is at least 14 nucleotides in length. A primer extension product may serve as a target nucleic acid template in subsequent extension reactions. A primer extension product may include a terminator.

As used herein, the terms "polynucleotide", "oligonucleotide", and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. The nucleotide monomer units may comprise any of the nucleotides described herein, including, but not limited to, specific nucleotides, nucleotide analogs, and universal nucleotides. Polynucleotides typically range in size from a few monomeric units, e.g. 5–40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Polynucleotides may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

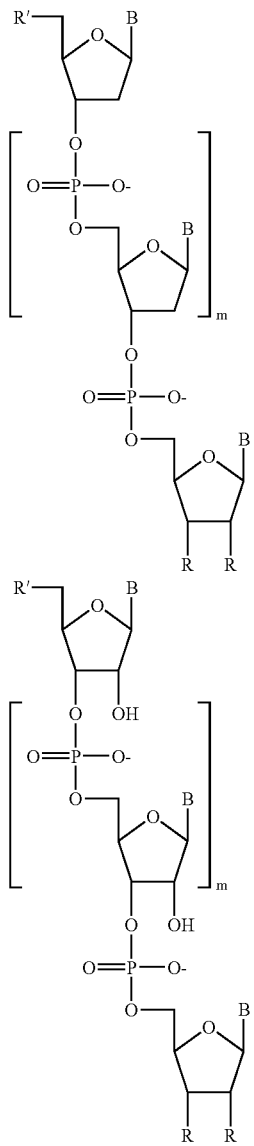

wherein each B is independently the base moiety of a nucleotide, e.g., a purine, a 7-deazapurine, a pyrimidine, a specific nucleotide, or a universal nucleotide; each m defines the length of the respective nucleic acid and can range from zero to thousands, tens of thousands, or even more; each R is independently selected from the group comprising hydrogen, hydroxyl, halogen, —R", —OR", and —NR"R", where each R" is independently ($C_1$–$C_6$) alkyl or ($C_5$–$C1_4$) aryl, or two adjacent Rs may be taken together to form a bond such that the ribose sugar is 2',3'-didehydroribose, and each R' may be independently hydroxyl or

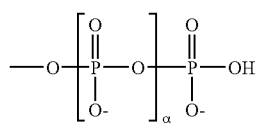

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably and, as used herein, refer to a polynucleotide that contains at least one nucleotide analog and/or at least one phosphate ester analog and/or at least one pentose sugar analog. Also included within the definition of polynucleotide analogs are polynucleotides in which the phosphate ester and/or sugar phosphate ester linkages are replaced with other types of linkages, such as N-(2-aminoethyl)-glycine amides and other amides (see, e.g., Nielsen et al., 1991, Science 254: 1497–1500; WO 92/20702; U.S. Pat. No. 5,719,262; U.S. Pat. No. 5,698,685;); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254: 1497–1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$–$C_4$ alkylphosphonate, e.g. methylphosphonate; (ii) phosphoramidate; (iii) $C_1$–$C_6$ alkylphosphotriester; (iv) phosphorothioate; and (v) phosphorodithioate.

The terms "annealing" and "hybridization" are used interchangeably and mean the base-pairing interaction of one nucleic acid with another nucleic acid that results in formation of a duplex, triplex, or other higher-ordered structure. When universal nucleotides are not involved, in certain embodiments, the primary interaction is base specific, e.g., A/T and G/C, by Watson/Crick and Hoogsteen-type hydrogen bonding. Base-stacking and hydrophobic interactions may also contribute to duplex stability.

The term "variant" as used herein refers to any alteration of a protein, including, but not limited to, changes in amino acid sequence, substitutions of one or more amino acids, addition of one or more amino acids, deletion of one or more amino acids, and alterations to the amino acids themselves. In certain embodiments, the changes involve conservative amino acid substitutions. Conservative amino acid substitution may involve replacing one amino acid with another that has, e.g., similar hydrophobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. The hydropathic index is discussed, e.g., in Kyte et al., J. Mol. Biol., 157:105–131 (1982). It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or nonnatural, that may be incorporated, either enzymatically or synthetically, into a polypeptide or protein.

As used herein, "mobility-dependent analysis technique" or "MDAT" means an analytical technique based on differential rates of migration among different analyte types. Exemplary mobility-dependent analysis techniques include electrophoresis, chromatography, mass spectroscopy, sedimentation, e.g., gradient centrifugation, field-flow fractionation, multi-stage extraction techniques, and the like.

As used herein, an "affinity set" is a set of molecules that specifically bind to one another. Affinity sets include, but are not limited to, biotin and avidin, biotin and streptavidin, receptor and ligand, antibody and ligand, antibody and antigen, and a polynucleotide sequence and its complement. One or more members of an affinity set may be coupled to a solid support. Exemplary solid supports include, but are not limited to, agarose, sepharose, magnetic beads, polystyrene, polyacrylamide, glass, membranes, silica, semiconductor materials, silicon, and organic polymers.

As used herein, "hybridization-based pullout", or "HBP", is a type of affinity separation wherein the affinity set is a polynucleotide sequence and its complement. HBP is a process wherein a nucleotide sequence is bound or immobilized to a solid support and is used to selectively adsorb its complement sequence (see, e.g., U.S. patent application Ser. No. 08/873,437 to O'Neill et al., filed Jun. 12, 1997).

Certain Exemplary Embodiments of the Invention

The present invention is directed to methods and kits for generating and analyzing primer extension products. Such primer extension products are generated by incubating a reaction composition comprising at least one universal nucleotide under appropriate conditions suitable for effecting primer extension. According to certain embodiments, the reaction composition comprises at least one terminator and at least one universal nucleotide. According to certain embodiments, the invention provides methods and kits for sequencing nucleic acids using a reaction composition comprising at least one universal nucleotide.

Exemplary Components

According to certain embodiments of the present invention, universal nucleotides comprise unnatural, predominantly hydrophobic bases that can pack efficiently in duplex DNA (see, e.g., Berger et al. Angew. Chem. Int. Ed. Engl. (2000) 39: 2940–42; Wu et al. J. Am. Chem. Soc. (2000) 122: 7621–32; Berger et al. Nuc. Acids Res. (2000) 28: 2911–14, Smith et al. Nucleosides & Nucleotides (1998) 17: 541–554, Ogawa et al. J. Am. Chem. Soc. (2000) 122: 3274–87). According to certain embodiments, a universal nucleotide may pair with two or more of the natural bases found in DNA. According to certain embodiments of the invention, universal nucleotides may lack the specific hydrogen bonding interaction of natural base pairs, and therefore may substitute for two or more bases in a DNA strand simply by steric and hydrophobic interactions.

According to certain embodiments of the invention, the universal nucleotides include, but are not limited to, 2'-deoxy-7-azaindole-5'-triphosphate (d7AITP), 2'-deoxy-isocarbostyril-5'-triphosphate (dICSTP), 2'-deoxy-propynyl-isocarbostyril-5'-triphosphate (dPICSTP), 2'-deoxy-6-methyl-7-azaindole-5'-triphosphate (dM7AITP), 2'-deoxy-imidizopyridine-5'-triphosphate (dImPyTp), 2'-deoxy-pyrrollpyrizine-5'-triphosphate (dPPTP), 2'-deoxy-allenyl-7-azaindole-5'-triphosphate (dA7AITP), or 2'-deoxy-propynyl-7-azaindole-5'-triphosphate (dP7AITP). In certain embodiments, the universal nucleotides are utilized by a polymerase, e.g., a DNA polymerase, at a rate nearly equal to the rate at which specific nucleotides are incorporated.

Certain embodiments of the invention employ a polymerase that has been optimized for use with universal nucleotides. According to certain embodiments, methods of optimizing a polymerase include, but are not limited to, site-directed mutagenesis, nonspecific mutagenesis, deletion of one or more amino acids, addition of one or more amino acids, substitution of one or more amino acids, and post-translational modifications, which include, but are not limited to, proteolysis, deletion of carbohydrate groups or phosphates, and addition of carbohydrate groups or phosphates. Thus, polymerases include naturally-occurring polymerases and modified polymerases or variant polymerases, including those modified for optimal incorporation of universal nucleotides.

According to certain embodiments, a polymerase incorporates universal nucleotides into a primer extension product at a rate that is at least 10% of the rate at which specific nucleotides are incorporated by the same polymerase. In certain embodiments, universal nucleotides are incorporated by polymerase at a rate that is at least 25% the rate at which specific nucleotides are incorporated by the same polymerase. In certain embodiments, universal nucleotides are incorporated at a rate that is at least 50% the rate at which specific nucleotides are incorporated. In certain embodiments, universal nucleotides are incorporated at a rate that is at least 75% the rate at which specific nucleotides are incorporated. In certain embodiments, polymerase incorporates universal nucleotides into a primer extension product at a rate that is equal to, or substantially equal to, the rate at which specific nucleotides are incorporated. According to certain embodiments, polymerase incorporates universal nucleotides at a rate that is sufficient to reduce premature chain termination.

Polymerases for use in the invention may or may not be thermostable. In certain embodiments, polymerases have mutations that reduce discrimination against the incorporation of chain terminators that are 3'-dideoxynucleotides as compared with nucleotide triphosphates. In certain embodiments, one can use mutants having a Tyr residue at position 667 (numbered with reference to Taq DNA polymerase). A detailed description of such mutants can be found, e.g., in U.S. Pat. No. 5,614,365. Such mutant polymerases may conveniently be referred to collectively as Y667 mutants.

According to certain embodiments, polymerases include, but are not limited to, DNA polymerase, RNA polymerase, reverse transcriptase, T7 polymerase, SP6 polymerase, T3 polymerase, Sequenase, Klenow fragment, AmpliTaq FS, a thermostable DNA polymerase with minimal or no 3'-5' exonuclease activity, or an enzymatically active variant or fragment of any of the above polymerases. According to certain embodiments of the invention, a mixture of two or more polymerases are used.

Primer Extension

Primer extension reactions according to certain embodiments, are used to make a complementary copy of at least a portion of a target nucleic acid template. In certain primer extension reactions, one uses an extension reaction composition comprising a target nucleic acid template, at least one primer, at least one universal nucleotide, and at least one polymerase. The at least one primer anneals to the target template. A primer extension product is generated when the polymerase enzymatically adds one or more nucleotides to the 3' end of the primer that is annealed to the target nucleic acid template.

The primer extension reaction may contain a combination of specific nucleotides and universal nucleotides, or it may contain exclusively universal nucleotides. The nucleotide that is added to the 3' end of the primer (or the 3' end of the primer extension product being extended from the primer) by polymerase may be a specific nucleotide, such that it is added in a template sequence-specific manner and pairs specifically with the template nucleotide opposite it. Alternatively, the nucleotide that is added by polymerase may be a universal nucleotide, which is added in a non-template sequence-specific manner. The polymerase adds nucleotides to the 3' end of the growing primer extension product until it reaches the end of the target nucleic acid template, or until it prematurely terminates before the end of the target nucleic acid template, e.g., by falling off the template, or by incorporation of a terminator, if present.

The result of the primer extension reaction is a primer extension product, which comprises the primer at its 5' end, covalently linked to a string of nucleotides that have been incorporated by polymerase. In certain embodiments, the string of nucleotides may comprise exclusively universal nucleotides of one type, or may comprise exclusively universal nucleotides of more than one type. In certain exemplary embodiments, the string of nucleotides may comprise a single type of universal nucleotide that pairs with A, T, C, and G. In certain exemplary embodiments, the string of nucleotides may comprise one type of universal nucleotide that pairs with C and G and another type of universal nucleotide that pairs with A and T. In certain exemplary embodiments, the string of nucleotides may comprise two different types of universal nucleotides that pair with A, T, C, and G. In certain embodiments, the string of nucleotides may comprise a combination of universal nucleotides of one type and specific nucleotides of one or more pairing types. In certain exemplary embodiments, the string of nucleotides may comprise a universal nucleotide that pairs with C and G in the template, and specific nucleotides A and T, which pair with T and A in the template, respectively. In certain embodiments, the string of nucleotides may comprise a combination of universal nucleotides of more than one type and specific nucleotides of one or more pairing types. In an exemplary case, the string of nucleotides may comprise two types of universal nucleotides, one which pairs with C and G, and the other which pairs with G and A, and specific nucleotide A, which pairs with T in the template.

According to certain embodiments, the primer extension reaction is part of a polymerase chain reaction (PCR). A general description of PCR is provided, e.g., in PCR Protocols: A Guide to Methods and Applications, Academic Press, New York, N.Y. (1990); and in PCR Primers: A Laboratory Manual, Cold Spring Harbor Laboratory Press, NY (1995). In PCR, the reaction composition includes at least one template, at least one primer, at least one polymerase, and extendable nucleotides. At least one universal nucleotide is included in the reaction composition. The reaction composition is subjected to cycles of temperature changes which result in a primer extension reaction that generates a primer extension product complementary to at least a portion of the target template, separation of the primer extension reaction product from the template, annealing of a new primer to at least a portion of the template and/or to the primer extension product, and subsequent primer extension reactions that generate primer extension products complementary to at least a portion of the template and/or complementary to at least a portion of the previously generated primer extension products.

In certain embodiments, the reaction composition contains one or more "primer sets", which comprise a forward primer and a reverse primer that anneal to opposite strands of the same double-stranded template. The forward primer anneals to one strand of the template, and the reverse primer anneals to the other strand of the template, such that the primer extension product from a forward primer comprises a sequence that is complementary to at least a portion of the primer extension product from the reverse primer. In subsequent primer extension reactions, the forward primer may anneal to the primer extension product from the reverse primer, and the reverse primer may anneal to the primer extension product from the forward primer.

Asymmetric PCR (A-PCR) according to the present invention comprises an amplification reaction composition wherein (i) at least one primer set comprises only a forward primer or only a reverse primer; (ii) there is an excess of one primer (relative to the other primer in a primer set); or (iii) at least one primer set wherein the $Tm_{50}$ of the first primer is at least 6–8° C. different from the $Tm_{50}$ of the second primer. In certain embodiments, the $Tm_{50}$ of the first primer is at least 10–12° C. different from the $Tm_{50}$ of the second primer. Consequently, following a primer extension reaction, an excess of products that are complementary to at least a portion of one strand of the template are generated relative to products that are complementary to at least a portion of the other strand of the template.

In certain embodiments of the invention, the asymmetric PCR reaction composition comprises at least one primer set having at least one forward primer, or at least one reverse primer, but typically not both. In such embodiments, primer extension reactions typically produce primer extension products that are complementary to at least a portion of one strand of the template, but not products complementary to at least a portion of the other strand. In each subsequent round of primer extension reaction, a new primer anneals to the template to produce a primer extension product. In certain embodiments, only the template, and not the primer extension product, is amplified in each subsequent round of asymmetric PCR.

In certain embodiments, the invention provides methods of asynchronous PCR. (See, e.g., U.S. patent application Ser. No. 09/875,211, filed Jun. 5, 2001.)

In certain embodiments, one can amplify multiple target sequences simultaneously using multiple sets of one or more primers specific for each of the target sequences, which may be referred to as multiplex PCR. (See, e.g., H. Geada et al., Forensic Sci. Int. 108:31–37 (2000) and D. G. Wang et al., Science 280:1077–82 (1998)).

Microsatellites, including STRs and VNTRs, are regions in the genome that contain a tandem array of a repeated sequence. The number of repeats may vary from individual to individual, or may be a marker for disease, and therefore these regions may be used for diagnostic purposes. The repeated sequence can be from 2 to about 80 nucleotides long, and the number of repeats ranges into the hundreds. The analysis of microsatellites, including STRs, typically requires precise determination of the number of repeats, and the difference in repeat number between two target nucleic acid templates can be as little as one or two.

In certain embodiments, STRs are analyzed by first amplifying the repeat region using PCR, with primers that flank the repeat region. The amplified primer extension products are then separated based on size. By analyzing the size of the products, one can determine the number of repeats in the STR being analyzed. In certain embodiments, one can analyze more than one STR region in the same reaction composition by using different labeled primers for each different STR region.

In certain embodiments, a reaction composition comprises at least one polymerase, at least one primer set, at least one target nucleic acid template, and at least one universal nucleotide. The reaction composition may or may not contain specific nucleotides. In certain embodiments, at least one primer in each primer set comprises a label. In certain embodiments, different primers for different templates have different labels.

In the primer extension reaction, polymerase adds nucleotides to the 3' end of the primer or primer extension product. In certain embodiments, specific nucleotides are added to the 3' end of the primer extension product according to the sequence of the template, while universal nucleotides are added non-specifically. In certain embodiments, the resulting primer extension product contains the primer sequence at its 5' end, covalently linked to a string of nucleotides that have been incorporated by polymerase. In certain embodiments, the string of nucleotides may comprise exclusively universal nucleotides of one type, or may comprise exclusively universal nucleotides of more than one type. In certain embodiments, the string of nucleotides may comprise a combination of universal nucleotides of one type and specific nucleotides of one or more pairing types, or may comprise a combination of universal nucleotides of more than one type and specific nucleotides of one or more pairing types.

In certain embodiments, the primer extension products may be separated by a mobility-dependent analysis technique, or MDAT. In certain embodiments, the primer extension products may be separated based on, e.g., molecular weight, length, sequence, and/or charge. Any method that allows two or more nucleic acid sequences in a mixture to be distinguished, e.g., based on mobility, length, molecular weight, sequence and/or charge, is within the scope of the invention. Exemplary MDAT techniques include, without limitation, electrophoresis, such as gel or capillary electrophoresis, HPLC, mass spectroscopy, including MALDI-TOF, and gel filtration. In certain embodiments, the MDAT is electrophoresis or chromatography.

In certain embodiments, the identity of the label that is attached to a primer extension product correlates with the identity of the primer, and therefore correlates with the identity of the template to which it anneals, and, thus the identity of the region being analyzed. Also, by separating the primer extension products, one may determine the number of repeats in a given STR. In this manner, the primer extension products of several different primer sets and target nucleic acid templates may be compared in a single primer extension reaction.

In various embodiments, different numbers of pairing types of specific nucleotides may be employed. In certain embodiments, the reaction composition comprises four specific extendable nucleotides and at least one universal nucleotide. In certain embodiments, the reaction composition comprises three specific extendable nucleotides and at least one universal nucleotide. In certain embodiments, the reaction composition comprises two specific extendable nucleotides and at least one universal nucleotide. In certain embodiments, the reaction composition comprises one specific extendable nucleotide and at least one universal nucleotide.

In certain such embodiments, the polymerase incorporates the specific extendable nucleotides and the at least one universal nucleotide into the primer extension product. In certain embodiments, at least some of the time, the at least one universal nucleotide, rather than a specific nucleotide, is incorporated by polymerase opposite one or more of the specific nucleotides in the template sequence.

In certain embodiments, the reaction composition comprises no specific extendable nucleotides, and at least one universal nucleotide. The at least one universal nucleotide is incorporated by polymerase into the primer extension product opposite all of the specific nucleotides in the template.

In certain embodiments of the invention, STRs are analyzed by asymmetric PCR. In certain embodiments of the invention, the reaction composition contains one or more primer sets, each of which contains only a forward or only a reverse primer. In certain embodiments, each different primer comprises a different label. In certain embodiments, the primer extension reaction for at least one primer set results in primer extension products that are complementary to only one strand of the template.

In certain embodiments of the invention, the primer is an oligonucleotide primer and the polynucleotide molecule for analysis is genomic DNA or cDNA. In certain embodiments, annealing the primer and the template, or duplex formation, may take place by hybridization. The primer/template duplex may contain one or more mismatches that do not significantly interfere with the ability of a polymerase to extend the primer or interfere with the ability of the 3' terminus nucleotide base of the primer to hybridize immediately adjacent to a predetermined location on the target nucleic acid template.

In certain embodiments, the initial target nucleic acid template is processed prior to amplifying it in the presence of universal nucleotides. In certain embodiments, the initial target nucleic acid template is processed to create a nucleic acid that comprises an STR and a constant length flanking region on one or both ends of the STR. In certain embodiments, such processed nucleic acids may be used as target nucleic acid templates in subsequent extension reactions to create extension products that have constant length flanking regions on both ends of the STR and that vary in length by the number of nucleotides in the STR.

In certain embodiments, the initial target nucleic acid template is processed by subjecting it to initial cycles of PCR in a first reaction composition comprising specific nucleotides and not comprising universal nucleotides. The resulting first primer extension products are then amplified in the presence of universal nucleotides. In certain embodiments, one or more initial cycles of PCR are performed with a first reaction composition that comprises specific nucleotides and both forward and reverse primers that flank each STR region, but that does not comprise universal nucleotides. Such initial cycles generate various first primer extension products that comprise flanking regions of predetermined length and the STR region. In certain embodiments, such first primer extension products serve as target nucleic acid templates for subsequent cycles of PCR with a second reaction composition that comprises at least one universal nucleotide and at least one primer. Such subsequent cycles and the remainder of the methods for detecting STRs, including separating and detecting of the second extension products, may be carried out as discussed above.

In certain embodiments, most or all of the initial target nucleic acid templates are removed prior to subsequent cycles of PCR with a reaction composition that comprises at least one universal nucleotide, and the first primer extension products serve as templates in such subsequent cycles of PCR. In certain embodiments, the initial target nucleic acid templates are modified with a first member of an affinity set.

In certain embodiments, the initial target nucleic acid templates are bound to a second member of the affinity set before, during, or after the initial cycles of PCR without universal nucleotides. In certain embodiments, the second member of the affinity set is coupled to a solid support so that most or all of the initial target nucleic acid templates may be separated from the reaction composition before the subsequent cycles of PCR with the at least one universal nucleotide. In certain embodiments, most or all of the initial target nucleic acid templates are removed with hybridization-based pull-out (HBP).

In certain embodiments, the initial target nucleic acid template is processed by digestion with restriction endonucleases prior to amplification in the presence of universal nucleotides. In certain embodiments, one or more initial target nucleic acid templates comprise one or more STR regions. The initial target nucleic acid templates are digested with one or more restriction endonucleases prior to amplification of the STR region by PCR in the presence of universal nucleotides. In certain embodiments, the initial target nucleic acid templates are digested in one or both regions flanking each STR region that is to be amplified to obtain target nucleic acid templates with constant length flanking regions on one or both ends of the STR. Such digested target nucleic acid templates can then be used in extension reactions to obtain primer extension products that have constant length flanking regions on both ends of the STR. The remainder of the methods for detecting STRs, including separating and detecting of the primer extension products, may be carried out as discussed above.

Analysis of microsatellites may be difficult if there is secondary structure present during an MDAT, e.g., electrophoresis, mass spectroscopy, or chromatography, which can cause aberrant mobility of the amplified products. According to certain embodiments, by replacing one or more of the extendable nucleotides in the primer extension reaction with one or more universal nucleotides, secondary structure formation during separation may be reduced. According to certain embodiments, longer repeat regions than microsatellite regions within the genome may be analyzed using universal nucleotides in the primer extension reaction, e.g., as part of a PCR reaction. STRs and methods of analyzing them are described, e.g., in U.S. Pat. Nos. 5,364,759, 5,075, 217, 6,090,558 and 6,221,598, which are herein incorporated by reference for any purpose.

The sequence of a nucleic acid may be determined by the creation of a primer extension product, e.g., by the method of Sanger (see, e.g., Sanger et al. *Proc. Nat. Acad. Sci* 74: 5463–5467 (1977)). According to certain embodiments, the present invention provides methods for sequencing nucleic acids using universal nucleotides in the reaction composition. In certain embodiments, a duplex (double stranded polynucleotide) is formed between a target nucleic acid template and a primer. The primer hybridizes to a predetermined location on the target nucleic acid template. In certain embodiments, one or more extendable nucleotides, including at least one universal nucleotide, one or more polymerases, and one or more specific terminators are included in the reaction composition with the primer. The reaction composition may or may not contain specific nucleotides.

The reaction composition is incubated under appropriate reaction conditions, such that one or more extendable nucleotides are incorporated sequentially by polymerase onto the 3' end of the primer. Specific nucleotides, if present, are added by polymerase in a template sequence-specific manner, while universal nucleotides are added in a non-template sequence-specific manner. A specific terminator may be incorporated into the primer extension product, and once incorporated, prevents further incorporation of nucleotides to the 3' end of the primer extension product by polymerase. The primer extension products generated by the primer extension reaction may then be separated based on size, and the sequence of the nucleic acid template can be determined from the particular sizes of the products and the identity of the specific terminator on each product.

In certain embodiments, the reaction composition contains four different specific terminators, e.g., A terminators, T terminators, G terminators, and C terminators, each of which is coupled to a different label. Each of the primer extension products that are generated therefore contains one of the four specific terminators at its 3' end, and the identity of this terminator correlates with the identity of the label. Furthermore, the identity of the nucleotide on the template strand opposite the terminator can be determined by the identity of the terminator (and therefore, the identity of the label). For example, if a primer extension product has a C terminator at its 3' end, then the template contains a G opposite the terminator. The length of the primer extension product determines where in the template sequence the G is located.

In certain embodiments using at least one universal nucleotide, the primer in the reaction composition further comprises a label and the terminators are not labeled. In certain embodiments, each of four different reaction compositions includes a primer that anneals to the same location on the template, but the primer in each of the different reaction compositions comprises a different label. The primer hybridizes to a predetermined location on the target nucleic acid template.

In certain embodiments, one or more extendable nucleotides, including at least one universal nucleotide, one or more polymerases, and one or more specific terminators are included in the reaction composition. In certain embodiments, a different unlabeled terminator is included in each of the four reaction compositions. The reaction composition may or may not contain specific nucleotides. The reaction composition is incubated under appropriate reaction conditions, such that one or more extendable nucleotides are incorporated sequentially by polymerase onto the 3' end of the primer. Specific nucleotides, if present, are added by polymerase in a template sequence-specific manner, while universal nucleotides are added in a non-specific manner.

In certain of those embodiments, each primer extension reaction generates primer extension products that have only one type of terminator at their 3' ends. The identity of the label that is coupled to the primer correlates to the identity of the terminator, and therefore the identity of the nucleotide opposite the terminator on the template. In certain embodiments, the primer extension products from the four separate reactions may be combined. The products may then be analyzed by an MDAT, e.g., separated based on size. The sequence of the template may then be determined from the particular sizes of the products and the identity of the terminator of each product.

In certain embodiments, more than one template may be sequenced in the same reaction composition. In certain embodiments, a reaction composition may contain two different primers that anneal to two different templates, each of the different primers comprising a different label. In certain embodiments, the reaction composition may further comprise four different terminators, each comprising a different label. In certain embodiments, one or more extendable nucleotides, including at least one universal nucleotide, and one or more polymerases are also included in the reaction composition. The reaction composition may or may not contain specific nucleotides. The reaction composition is incubated under appropriate reaction conditions, such that one or more extendable nucleotides are incorporated sequentially by polymerase onto the 3' end of each of the different primers, according to the template sequence to which each primer anneals. Specific nucleotides, if present, are added by polymerase in a template sequence-specific manner, while universal nucleotides are added in a non-specific manner.

The primer extension reaction, therefore, generates primer extension products that each have a label that identifies the primer that was extended, and another label that identifies the terminator at the 3' end. In certain embodiments, the primer extension products may be separated. The sequence of the template may be determined from the particular sizes of the products, the identity of the primer, and the identity of the terminator of each product. Therefore, the sequence of each of the two templates may be determined simultaneously.

In certain embodiments, the reaction composition may contain more than two different primers, each comprising a different label, that anneal to different templates. In certain embodiments, the reaction composition contains the different labeled primers and four different terminators, each comprising a different label. In certain embodiments, the reactions are carried out substantially as described above for two different primers.

In certain embodiments, a reaction composition may comprise one type of unlabeled terminator and two or more different labeled primers that are specific for two or more different templates. In certain embodiments, four different reaction compositions each comprise a different unlabeled terminator and the two or more different labeled primers. In certain embodiments, each reaction composition is then subjected to a primer extension reaction. The extension product of each reaction composition is then separated. The label will indicate which template correlates to the extension product. The identity of the terminated nucleotide, and thus, the identity of the template nucleotide opposite it, can be determined based on the reaction composition from which the primer extension product was generated. The length of the product will indicate where the nucleotide is included in the template.

In various embodiments, different numbers of pairing types of specific nucleotides may be employed. In certain embodiments, the reaction composition comprises four specific extendable nucleotides and at least one universal nucleotide. In certain embodiments, the reaction composition comprises three specific extendable nucleotides and at least one universal nucleotide. In certain embodiments, the reaction composition comprises two specific extendable nucleotides and at least one universal nucleotide. In certain embodiments, the reaction composition comprises one specific extendable nucleotide and at least one universal nucleotide.

In certain such embodiments, the polymerase incorporates the specific extendable nucleotides and the at least one universal nucleotide into the primer extension product. In certain embodiments, at least some of the time, the at least one universal nucleotide, rather than a specific nucleotide, is incorporated by polymerase opposite one or more of the specific nucleotides in the template sequence.

In certain embodiments, the reaction composition comprises no specific extendable nucleotides, and at least one universal nucleotide. The at least one universal nucleotide is incorporated by polymerase into the primer extension product opposite all of the specific nucleotides in the template.

In certain embodiments, the primer extension products may be separated by a mobility-dependent analysis technique, or MDAT. In certain embodiments, the primer extension products may be separated based on, e.g., molecular weight, length, sequence, and/or charge. Any method that allows two or more nucleic acid sequences in a mixture to be distinguished, e.g., based on mobility, length, molecular weight, sequence and/or charge, is within the scope of the invention. Exemplary separation techniques include, without limitation, electrophoresis, such as gel or capillary electrophoresis, HPLC, mass spectroscopy, including MALDI-TOF, and gel filtration. In certain embodiments, the MDAT is electrophoresis or chromatography. By separating the primer extension products, one can determine the sequence of the template nucleic acid based on the size of each product and the identity of the terminator at its 3' end.

In certain embodiments of the invention, the primer is an oligonucleotide primer and the polynucleotide molecule for analysis is genomic DNA or cDNA. In certain embodiments, annealing the primer and the template, or duplex formation, may take place by hybridization. The primer/template duplex may contain one or more mismatches that do not significantly interfere with the ability of a polymerase to extend the primer or interfere with the ability of the 3' terminus nucleotide base of the primer to hybridize immediately adjacent to a predetermined location on the target nucleic acid template.

In certain embodiments, the methods include cycle sequencing, in which, following the primer extension reaction and termination, the primer extension product is released from the target nucleic acid template, and a new primer is annealed, extended, and terminated in the same manner. Cycle sequencing allows amplification of the primer extension products. In certain embodiments, cycle sequencing is performed using a thermocycler apparatus.

In certain embodiments, the primer and/or the terminator is labeled. In certain embodiments, the label comprises a fluorescent dye. In certain embodiments, the reaction contains four different terminators, each labeled with a different fluorescent dye. In certain embodiments, four reaction compositions each contain a primer that is labeled with a different fluorescent dye. In certain embodiments, the four primers have the same sequence. In certain embodiments, one reaction composition contains more than one different primer, and each different primer is labeled with a different fluorescent dye. In certain embodiments, the primer extension products are separated, e.g. by electrophoresis, mass spectroscopy, or chromatography.

DNA sequencing technology may be limited by variability that can result from the differences between the four specific bases of DNA. For example, during separation of the sequencing products, compressions may result from secondary structure that occurs in regions of high G-C content. These compressions can cause multiple products to run at the same size, resulting in several primer extension product peaks overlapping following electrophoresis, mass spectroscopy, or chromatography. In certain embodiments, the present invention provides methods that may reduce secondary structure in primer extension products, thereby reducing compressions, by replacing one or more of the dNTPs in the sequencing reaction with at least one universal nucleotide.

Also, the use of at least one universal nucleotide according to certain embodiments may reduce premature chain termination in an extension reaction. Premature chain termination is termination of the extension reaction prior to incorporation of a terminator in the extension product.

Kits

The invention also provides kits for performing the foregoing methods. In certain embodiments, kits serve to expedite the performance of the methods of interest by assembling two or more components used to carry out the methods. In certain embodiments, kits contain components in pre-measured unit amounts to minimize the need for measurements by end-users. In certain embodiments, kits include instructions for performing one or more methods of the invention. In certain embodiments, the kit components are optimized to operate in conjunction with one another.

In certain embodiments, the kits of the invention may be used to sequence at least one target nucleic acid template. In certain embodiments, the kits for sequencing target nucleic acid templates include at least one universal nucleotide, at least one polymerase, and at least one specific terminator. In certain embodiments, kits for sequencing target nucleic acid templates may contain additional components, including, but not limited to, at least one primer. In certain embodiments, the at least one specific terminator and/or the at least one primer may further comprise a label. Kits may also include the reagents for performing a control reaction, which may include one or more of the above components, and at least one target nucleic acid template.

In certain embodiments, the kits of the invention may be used to generate a plurality of primer extension products. In certain embodiments, the kits may be used for STR analysis. In certain embodiments, kits for STR analysis include at least one universal nucleotide and at least one polymerase. In certain embodiments, kits for STR analysis may include at least one primer. In certain embodiments, the at least one primer may further comprise a label. Kits for STR analysis may also include the reagents for performing a control reaction, which may include one or more of the above components, and at least one target nucleic acid template.

Other embodiments of the invention will be apparent to those skilled in the art from consideration of the specification and practice of the invention disclosed herein. It is intended that the specification and examples be considered as exemplary only.

What is claimed is:

1. A kit for sequencing a target nucleic acid template, comprising at least one universal nucleotide, at least one polymerase, and at least one specific terminator; wherein one or more of the at least one universal nucleotides is individually selected from 2'-deoxy-7-azaindole-5'-triphosphate (d7AITP), 2'-deoxy-isocarbostyril-5'-triphosphate (dICSTP), 2'-deoxy-propynylisocarbostyril-5'-triphosphate (dPICSTP), 2'-deoxy-6-methyl-7-azaindole-5'-triphosphate (dM7AITP), 2'-deoxy-imidizopyridine-5'-triphosphate (dImPyTp), 2'-deoxy-pyrrollpyrizine-5'-triphosphate (dPPTP), 2'-deoxy-allenyl-7-azaindole-5'-triphosphate (dA7AITP), and 2'-deoxy-propynyl-7-azaindole-5'-triphosphate (dP7AITP).

2. The kit of claim 1, wherein one or more of the at least one specific terminators comprises a label.

3. The kit of claim 2, wherein the label comprises a fluorescent dye.

4. The kit of claim 3, wherein the label comprises an energy-transfer fluorescent dye.

5. The kit of claim 1, further comprising at least one primer.

6. A kit for detecting a short tandem repeat in a target nucleic acid template, comprising at least one universal nucleotide, at least one polymerase, and at least one primer comprising a sequence that is complementary to a sequence adjacent to a short tandem repeat in the target nucleic acid template; wherein one or more of the at least one universal nucleotides is individually selected from 2'-deoxy-7-azaindole-5'-triphosphate (d7AITP), 2'-deoxy-isocarbostyril-5'-triphosphate (dICSTP), 2'-deoxy-propynylisocarbostyril-5'-triphosphate (dPICSTP), 2'-deoxy-6-methyl-7-azaindole-5'-triphosphate (dM7AITP), 2'-deoxy-imidizopyridine-5'-triphosphate (dImPyTp), 2'-deoxy-pyrrollpyrizine-5'-triphosphate (dPPTP), 2'-deoxy-allenyl-7-azaindole-5'-triphosphate (dA7AITP), and 2'-deoxy-propynyl-7-azaindole-5'-triphosphate (dP7AITP).

7. The kit of claim 6, wherein one or more of the at least one primers comprises a label.

8. The kit of claim 7, wherein the label comprises a fluorescent dye.

9. The kit of claim 8, wherein the label comprises an energy-transfer fluorescent dye.

10. The kit of claim 6, wherein the at least one primer is two primers.

* * * * *

UNITED STATES PATENT AND TRADEMARK OFFICE
CERTIFICATE OF CORRECTION

PATENT NO. : 7,169,557 B2 Page 1 of 1
APPLICATION NO. : 10/290672
DATED : January 30, 2007
INVENTOR(S) : Rosenblum et al.

It is certified that error appears in the above-identified patent and that said Letters Patent is hereby corrected as shown below:

Title page, item (*) Notice: Delete "431 days" and insert --388 days--.

Signed and Sealed this

Thirteenth Day of November, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 12
<212> TYPE: DNA
<213> ORGANISM: Artificial Sequence
<220> FEATURE:

```
<223> OTHER INFORMATION: hypothetical DNA template

<400> SEQUENCE: 1
cgtacgtacg ta                                                              12

<210> SEQ ID NO 2
<211> LENGTH: 12
<212> TYPE: DNA
<213> ORGANISM: Artificial Sequence
<220> FEATURE:
<223> OTHER INFORMATION: hypothetical primer extension product

<400> SEQUENCE: 2
tacgtacgta gc                                                              12

<210> SEQ ID NO 3
<211> LENGTH: 12
<212> TYPE: DNA
<213> ORGANISM: Artificial Sequence
<220> FEATURE:
<223> OTHER INFORMATION: hypothetical primer extension product
<220> FEATURE:
<221> NAME/KEY: misc_feature
<222> LOCATION: (4)..(12)
<223> OTHER INFORMATION: n equals exemplary universal nucleotide "X"

<400> SEQUENCE: 3
tacgnnnnnn nn                                                              12

<210> SEQ ID NO 4
<211> LENGTH: 12
<212> TYPE: DNA
<213> ORGANISM: Artificial Sequence
<220> FEATURE:
<223> OTHER INFORMATION: hypothetical primer extension product
<220> FEATURE:
<221> NAME/KEY: misc_feature
<222> LOCATION: (7)..(12)
<223> OTHER INFORMATION: n equals exemplary universal nucleotide "Z"

<400> SEQUENCE: 4
tacgtannta nn                                                              12

<210> SEQ ID NO 5
<211> LENGTH: 12
<212> TYPE: DNA
<213> ORGANISM: Artificial Sequence
<220> FEATURE:
<223> OTHER INFORMATION: hypothetical primer extension product
<220> FEATURE:
<221> NAME/KEY: misc_feature
<222> LOCATION: (5)..(12)
<223> OTHER INFORMATION: n equals exemplary universal nucleotide "Y"

<400> SEQUENCE: 5
tacgnncnnn cn                                                              12
```